United States Patent [19]

Baker et al.

[11] Patent Number: 4,569,937

[45] Date of Patent: Feb. 11, 1986

[54] ANALGESIC MIXTURE OF OXYCODONE AND IBUPROFEN

[75] Inventors: Geraldine L. Baker, Minneapolis, Minn.; William K. Schmidt, Wilmington, Del.

[73] Assignee: E. I. Du Pont de Nemours and Company, Wilmington, Del.

[21] Appl. No.: 700,654

[22] Filed: Feb. 11, 1985

[51] Int. Cl.$^4$ .................... A61K 31/19; A61K 31/44
[52] U.S. Cl. ................................ 514/282; 514/557
[58] Field of Search ........................................ 424/260

[56] References Cited

U.S. PATENT DOCUMENTS 4,322,427  3/1982  Buyniski et al. .
4,489,080  12/1984  Loman ............................... 424/260

FOREIGN PATENT DOCUMENTS 0068838  1/1983  European Pat. Off. .

OTHER PUBLICATIONS

S. A. Cooper et al., "Relative Efficacy of an Ibuprofen-Codeine Combination", Clin. Pharmacol. Ther., 27(2), 1980, p. 249.

AMA Drug Evaluations, Fifth Ed., 1983 Chapter 4, pp. 101–102.

Pharmacotherapy, 2, No. 3, May/Jun. 1982, Cooper et al.: Analgesic Efficacy of an Ibuprofen-Codeine Combination, pp. 162–167.

Clinical Pharmacology, K. L. Melmon, M.D., et al., Chap. 11, pp. 498–499, (1972).

The Pharmacological Basis of Therapeutics, L. S. Goodman et al., 5th Ed., Chap. 17, pp. 348–349, (1975).

*Primary Examiner*—Stanley J. Friedman

[57] ABSTRACT

Pharmaceutical compositions of narcotic analgesics and ibuprofen have been found to exhibit unexpectedly enhanced analgesic activity by applying an analysis model which considers data characterizing the analgesic effect of both the pure components as well as the fixed dose ratio combinations. This synergism enables the use of lower doses of either or both drugs with a concomitant reduction in risk of possible side effects.

6 Claims, 1 Drawing Figure

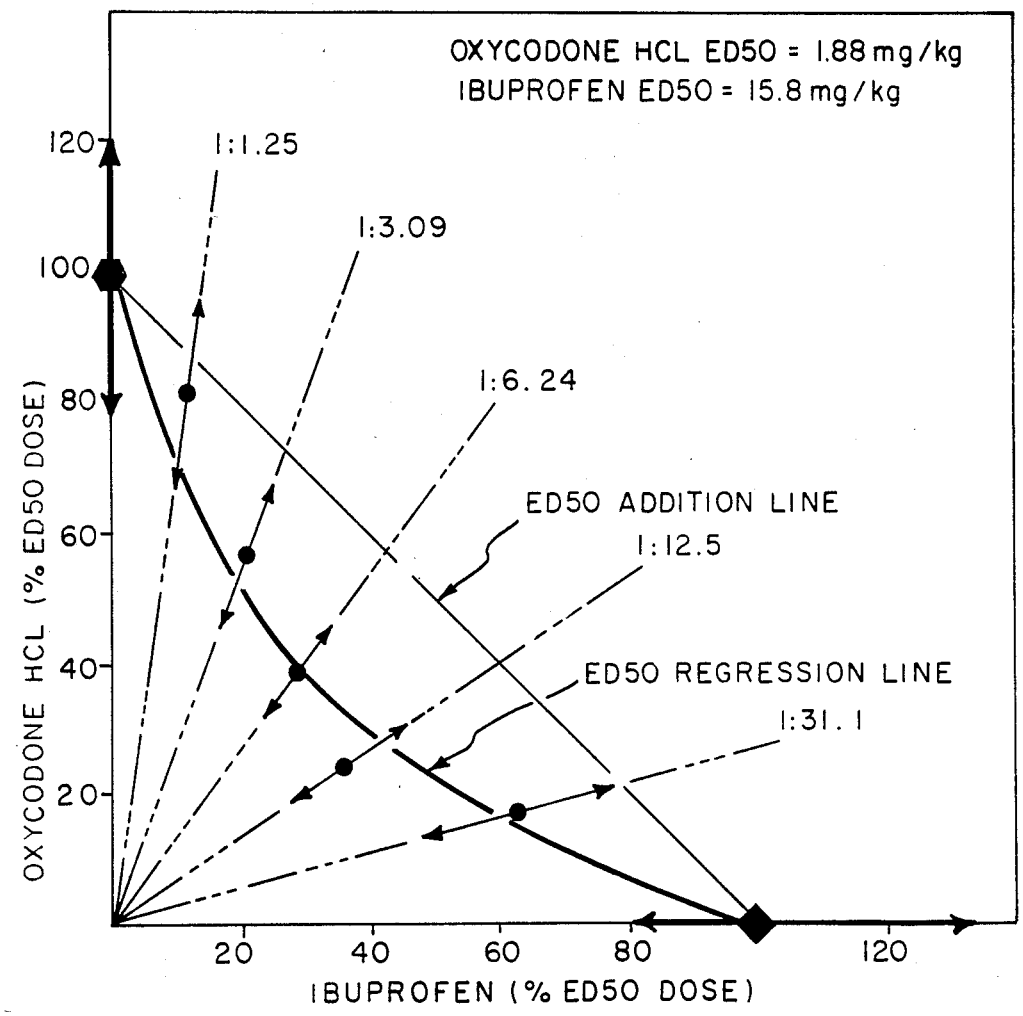

ANALGESIC MIXTURE OF OXYCODONE AND IBUPROFEN

TECHNICAL FIELD

This invention relates to pharmaceutical compositions of narcotic analgesics and ibuprofen having analgesic activity in mammals, and to methods of use of the compositions to alleviate pain in mammals.

BACKGROUND OF THE INVENTION

More active analgesic combinations are in constant demand because they offer the attractive possibility of relieving pain with reduced dosages thereby diminishing the expected side effects and toxicity that would result from the otherwise required higher dosages.

U.S. Pat. No. 4,464,376, issued to A. Sunshine et al., on Aug. 7, 1984 describes analgesic and antiinflammatory compositions which comprise caffeine together with a selected non-narcotic/non-steroidal antiinflammatory drug (NSAID) or a selected narcotic analgesic or both. This patent discloses that the analgesic effect of the combination of a selected NSAID and a selected narcotic analgesic is greater than for either alone which analgesic effect is further enhanced by the addition of caffeine. Sunshine provides no evidence or suggestion of other than an additive analgesic effect for the combinations.

S. Cooper et al., Pharmacotherapy, 2, 162 (1982), describe the analgesic efficacy of an ibuprofen/codeine combination in patients who had undergone dental impaction surgery. Codeine was found to add "a small amount of additional analgesia when used in combination with ibuprofen." This increase in analgesic effects was not statistically significant and there is no suggestion that the combination had a synergistic effect.

U.S. Pat. No. 4,237,140, issued to J. R. Dudzinski on Dec. 2, 1980, describes an analgesic mixture of nalbuphine and acetaminophen. U.S. Pat. No. 4,282,215, issued to J. R. Dudzinski and W. K. Schmidt on Aug. 4, 1981, describes an analgesic mixture of nalbuphine and aspirin. Other nalbuphine analgesic combinations are described in U.S. Pat. No. 4,366,159, issued to M. R. Magruder on Dec. 28, 1982 (with narcotics); U.S. Pat. No. 4,404,210, issued to W. K. Schmidt on Sept. 13, 1983 (with ibuprofen); U.S. Pat. No. 4,407,805, issued to W. K. Schmidt on Oct. 4, 1983 (zomepirac); U.S. Pat. No. 4,402,962, issued to W. K. Schmidt on Sept. 6, 1983 (4,5-bis(4-methoxyphenyl)-2-(trifluoromethylsulfonyl)-1H-imidazole); U.S. Pat. No. 4,407,804, issued to W. K. Schmidt on Oct. 4, 1983 (indomethacin); U.S. Pat. No. 4,404,208, issued to W. K. Schmidt on Sept. 13, 1983 (tiflamizole); U.S. Pat. No. 4,404,209, issued to W. K. Schmidt on Sept. 13, 1983 (sulindac); and U.S. Pat. No. 4,404,211, issued to W. K. Schmidt on Sept. 13, 1983 (flurbiprofen).

U.S. Pat. Nos. 3,228,831 and 3,385,886 issued to Nicholson and Adams disclose the synthesis, formulation, and analgesic properties of α-methyl-4-(2-methylpropyl)benzeneacetic acid, commonly called ibuprofen:

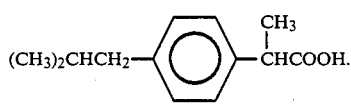

Adams et al., Arch. Pharmacodyn. Ther., 178, 115 (1969), further characterize the use of ibuprofen as an analgesic.

Narcotic analgesics are well known, strong analgesics which can, unfortunately, be addictive and subjected to abuse by parenteral administration. A continuing goal is to be able to reduce the dosage of such narcotic analgesics by combining them with non-addicting ingredients while still maintaining a high level of analgesia.

SUMMARY OF THE INVENTION

According to the present invention there is provided a pharmaceutical composition comprising a combination of (a) a narcotic analgesic, or a pharmaceutically acceptable salt thereof, and (b) ibuprofen, or a pharmaceutically suitable salt thereof, in which the weight ratio of (a):(b) is from about 1:1 to about 1:800. Preferred ratios of (a):(b) are from about 1:3 to about 1:400, and most preferred ratios are from about 1:30 to about 1:400.

Specifically, a pharmaceutical composition comprising a combination of synergistically effective analgesic amounts of oxycodone, or a pharmaceutically suitable salt thereof, and ibuprofen, or a pharmaceutically suitable salt thereof, has been found to provide enhanced pain relief in mammals.

Another aspect of the invention comprises a method of alleviating pain in a mammal by administering an effective analgesic amount of a composition described above to the mammal.

BRIEF DESCRIPTION OF THE DRAWING

The FIGURE is an isobologram plot characterizing effective pain relieving doses which produce analgesic responses in one half the mice subjected to the phenyl-p-benzoquinone induced writhing test at various dose ratios of oxycodone and ibuprofen.

DETAILED DESCRIPTION OF THE INVENTION

Narcotic analgesics are well known and have been used for many years for the treatment of moderate to severe pain. The term narcotic analgesic when used herein includes but is not limited to oxycodone, oxymorphone, hydrocodone, hydromorphone, morphine, meperidine, and methadone. Oxycodone, oxymorphone, hydrocodone and hydromorphone are preferred because of their strong potency in oral dosage forms. Oxycodone is most preferred.

Ibuprofen, which has the chemical name α-methyl-4-(2-methylpropyl)benzeneacetic acid, and its preparation are described in U.S. Pat. Nos. 3,228,831 and 3,385,886, the disclosures of which are hereby incorporated by reference.

When the terms narcotic analgesic or ibuprofen are used herein, it is to be understood that any of the pharmaceutically suitable salts thereof which have analgesic properties in man and other mammals are included by the term. For narcotic analgesics, such salts include the hydrochlorides, hydrobromides, hydroiodides, sulfates, bisulfates, nitrates, citrates, tartrates, bitartrates, phosphates, malates, maleates, fumarates, succinates, acetates, terephthalates, and pamoates, while for ibuprofen, pharmaceutically suitable salts would include those of aluminum, calcium, potassium, and sodium.

In a composition of the invention, oxycodone and ibuprofen are combined and have been utilized at dose ratios based on weight of oxycodone to ibuprofen of from 1:1.25 to 1:31.1 in mice subjected to the phenyl-p-benzoquinone induced writhing test to establish analgetic effectiveness. The phenyl-p-benzoquinone induced writhing test in mice [H. Blumberg et al., Proc. Soc. Exp. Biol. Med., 118, 763-766 (1965)] is a standard procedure for detecting and comparing the analgesic activity of different classes of analgesic drugs with a good correlation with human analgesic activity. Data for the mouse, as presented in the isobologram, can be translated to other species where the orally effective analgesic dose of the individual compounds is known or can be estimated. The method simply consists of reading the % ED50 DOSE for each dose ratio on the best fit regression analysis curve from the mouse isobologram, multiplying each component by its effective species dose, and then forming the ratio of the amount of oxycodone to ibuprofen. This basic correlation for analgesic properties enables estimation of the range of human effectiveness. [E. W. Pelikan, the Pharmacologist 1, 73 (1959).]

Application of an equieffective dose substitution model and a curvilinear regression analysis utilizing all the data for the individual compounds and various dose ratios for the combinations establishes the existence of unexpectedly enhanced analgesic activity of combinations of oxycodone and ibuprofen, i.e., the resulting activity is greater than the activity expected from the sum of the activities of the individual components.

Compositions of the invention present the opportunity of obtaining relief from pain with reduced dosages of narcotic analgesics, such as oxycodone, thereby diminishing the side effects and toxicity which would result from the otherwise required amounts of the individual drug components.

Dosage Forms

The combination of analgesic agents of the invention can be administered to treat pain by any means that produces contact of the active agent with the agent's site of action in the body of a mammal. The composition of the invention can be administered by any conventional means available for use in conjunction with pharmaceuticals. It can be administered alone, but is generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage can be such that the active ingredient is administered at a daily dosage of from about 0.05 to 7.50 milligrams per kilogram (mg/kg) of body weight of oxycodone and from about 10 to 120 mg/kg of ibuprofen. Ordinarily, administration of the composition of the invention in divided doses 2-5 times a day or in a sustained release form is effective to obtain desired results.

Dosage forms (compositions) suitable for internal administration contain a total of from about 5 milligrams to about 600 milligrams of active ingredients per unit. In these pharmaceutical compositions the active ingredients will ordinarily be present in an amount of about 0.5-95% by weight based on the total weight of the composition.

The active ingredients can be administered orally in solid dosage forms, such as capsules, tablets, and powders, or in liquid dosage forms, such as elixirs, syrups, and suspensions.

Gelatin capsules contain the active ingredients and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, A. Osol, a standard reference text in this field.

Useful pharmaceutical dosage-forms for administration of the composition of the invention can be illustrated by the following examples:

Eample 1

| Oxycodone/Ibuprofen Tablets Formula | (5/60 mg) mg/Tablet |
|---|---|
| Oxycodone HCl | 5.0 |
| Ibuprofen | 60.0 |
| Microcrystalline Cellulose | 140.0 |
| Starch, modified | 16.0 |
| Stearic Acid | 4.0 |
| | 225.0 |

Example 2

| Oxycodone/Ibuprofen Tablets Formula | (5/300 mg) mg/Tablet |
|---|---|
| Oxycodone HCl | 5.0 |
| Ibuprofen | 300.0 |
| Microcrystalline Cellulose | 190.0 |
| Starch, modified | 22.0 |
| Stearic Acid | 8.0 |
| | 525.0 |

Example 3

| Oxycodone/Ibuprofen Tablets Formula | (2.5/300 mg) mg/Tablet |
|---|---|
| Oxycodone HCl | 2.5 |
| Ibuprofen | 300.0 |
| Microcrystalline Cellulose | 212.5 |
| Starch, modified | 22.0 |
| Stearic Acid | 8.0 |
| | 545.0 |

Example 4

| Oxycodone/Ibuprofen Capsules Formula | (5/60 mg) mg/Capsule |
|---|---|
| Oxycodone HCl | 5.0 |
| Ibuprofen | 60.0 |
| Microcrystalline Cellulose | 140.0 |
| Starch, modified | 112.0 |
| Starch | 8.0 |

-continued

| Oxycodone/Ibuprofen Capsules Formula | (5/60 mg) mg/Capsule |
|---|---|
| | 325.0 |

Example 5

| Oxycodone/Ibuprofen Capsules Formula | (5/300 mg) mg/Capsule |
|---|---|
| Oxycodone HCl | 5.0 |
| Ibuprofen | 300.0 |
| Microscrystalline Cellulose | 90.0 |
| Starch, modified | 7.0 |
| Starch | 8.0 |
| | 410.0 |

Example 6

| Oxycodone/Ibuprofen Capsules Formula | (2.5/300 mg) mg/Capsule |
|---|---|
| Oxycodone HCl | 2.5 |
| Ibuprofen | 300.0 |
| Microcrystalline Cellulose | 110.0 |
| Starch, modified | 9.5 |
| Starch | 8.0 |
| | 430.0 |

Example 7

| Oxymorphone/Ibuprofen Tablets Formula | (5/60 mg) mg/Tablet |
|---|---|
| Oxymorphone HCl | 5.0 |
| Ibuprofen | 60.0 |
| Microcrystalline Cellulose | 140.0 |
| Starch, modified | 16.0 |
| Stearic Acid | 4.0 |
| | 225.0 |

Example 8

| Oxymorphone/Ibuprofen Formula | (5/300 mg) mg/Tablet |
|---|---|
| Oxymorphone HCl | 5.0 |
| Ibuprofen | 300.0 |
| Microcrystalline Cellulose | 190.0 |
| Starch, modified | 22.0 |
| Stearic Acid | 8.0 |
| | 525.0 |

Example 9

| Oxymorphone/Ibuprofen Formula | (2.5/300 mg) mg/Tablet |
|---|---|
| Oxymorphone HCl | 2.5 |
| Ibuprofen | 300.0 |
| Microcrystalline Cellulose | 212.5 |
| Starch, modified | 22.0 |
| Stearic Acid | 8.0 |
| | 545.0 |

Example 10

| Oxymorphone/Ibuprofen Capsules Formula | (5/60 mg) mg/Capsule |
|---|---|
| Oxymorphone HCl | 5.0 |
| Ibuprofen | 60.0 |
| Microcrystalline Cellulose | 140.0 |
| Starch, modified | 112.0 |
| Starch | 8.0 |
| | 325.0 |

Example 11

| Oxymorphone/Ibuprofen Capsules Formula | (5/300 mg) mg/Capsule |
|---|---|
| Oxymorphone HCl | 5.0 |
| Ibuprofen | 300.0 |
| Microcrystalline Cellulose | 90.0 |
| Starch, modified | 7.0 |
| Starch | 8.0 |
| | 410.0 |

Example 12

| Oxymorphone/Ibuprofen Capsules Formula | (2,5/300 mg) mg/Capsule |
|---|---|
| Oxymorphone HCl | 2.5 |
| Ibuprofen | 300.0 |
| Microcrystalline Cellulose | 110.0 |
| Starch, modified | 9.5 |
| Starch | 8.0 |
| | 430.0 |

Example 13

| Hydrocodone/Ibuprofen Tablets Formula | (5/60 mg) mg/Tablet |
|---|---|
| Hydrocodone Bitartrate | 5.0 |
| Ibuprofen | 60.0 |
| Microcrystalline Cellulose | 140.0 |
| Starch, modified | 16.0 |
| Starch | 4.0 |
| | 225.0 |

Example 14

| Hydrocodone/Ibuprofen Tablets Formula | (5/300 mg) mg/Tablet |
|---|---|
| Hydrocodone Bitartrate | 5.0 |
| Ibuprofen | 300.0 |
| Microcrystalline Cellulose | 190.0 |
| Starch, modified | 22.0 |
| Starch | 8.0 |
| | 525.0 |

Example 15

| Hydrocodone/Ibuprofen Tablets Formula | (2.5/300 mg) mg/Tablet |
|---|---|
| Hydrocodone Bitartrate | 2.5 |
| Ibuprofen | 300.0 |
| Microcrystalline Cellulose | 212.5 |
| Starch, modified | 22.0 |

-continued

| Hydrocodone/Ibuprofen Tablets Formula | (2.5/300 mg) mg/Tablet |
|---|---|
| Starch | 8.0 |
| | 545.0 |

Example 16

| Hydrocodone/Ibuprofen Capsules Formula | (5/60 mg) mg/Capsule |
|---|---|
| Hydrocodone Bitartrate | 5.0 |
| Ibuprofen | 60.0 |
| Microcrystalline Cellulose | 140.0 |
| Starch, modified | 112.0 |
| Starch | 8.0 |
| | 325.0 |

Example 17

| Hydrocodone/Ibuprofen Capsules Formula | (5/300 mg) mg/Capsule |
|---|---|
| Hydrocodone Bitartrate | 5.0 |
| Ibuprofen | 300.0 |
| Microcrystalline Cellulose | 90.0 |
| Starch, modified | 7.0 |
| Starch | 8.0 |
| | 410.0 |

Example 18

| Hydrocodone/Ibuprofen Capsules Formula | (2.5/300 mg) mg/Capsule |
|---|---|
| Hydrocodone Bitartrate | 2.5 |
| Ibuprofen | 300.0 |
| Microcrystalline Cellulose | 110.0 |
| Starch, modified | 9.5 |
| Starch | 8.0 |
| | 430.0 |

Example 19

| Hydromorphone/Ibuprofen Tablets Formula | (3/60 mg) mg/Tablet |
|---|---|
| Hydromorphone HCl | 3.0 |
| Ibuprofen | 60.0 |
| Microcrystalline Cellulose | 140.0 |
| Starch, modified | 18.0 |
| Stearic Acid | 4.0 |
| | 225.0 |

Example 20

| Hydromorphone/Ibuprofen Tablets Formula | (3/300 mg) mg/Tablet |
|---|---|
| Hydromorphone HCl | 3.0 |
| Ibuprofen | 300.0 |
| Microcrystalline Cellulose | 190.0 |
| Starch, modified | 24.0 |
| Stearic Acid | 8.0 |
| | 525.0 |

Example 21

| Hydromorphone/Ibuprofen Tablets Formula | (1.5/300 mg) mg/Tablet |
|---|---|
| Hydromorphone HCl | 1.5 |
| Ibuprofen | 300.0 |
| Microcrystalline Cellulose | 213.5 |
| Starch, modified | 22.0 |
| Stearic Acid | 8.0 |
| | 545.0 |

Example 22

| Hydromorphone/Ibuprofen Capsules Formula | (3/60 mg) mg/Capsule |
|---|---|
| Hydromorphone HCl | 3.0 |
| Ibuprofen | 60.0 |
| Microcrystalline Cellulose | 140.0 |
| Starch, modified | 114.0 |
| Starch | 8.0 |
| | 325.0 |

Example 23

| Hydromorphone/Ibuprofen Capsules Formula | (3/300 mg) mg/Capsule |
|---|---|
| Hydromorphone HCl | 3.0 |
| Ibuprofen | 300.0 |
| Microcrystalline Cellulose | 90.0 |
| Starch, modified | 9.0 |
| Starch | 8.0 |
| | 410.0 |

Example 24

| Hydromorphone/Ibuprofen Capsules Formula | (1.5/300 mg) mg/Capsule |
|---|---|
| Hydromorphone HCl | 1.5 |
| Ibuprofen | 300.0 |
| Microcrystalline Cellulose | 110.0 |
| Starch, modified | 10.5 |
| Starch | 8.0 |
| | 430.0 |

Test Methods

The unexpectedly enhanced analgesic activity obtained in the method of the invention is evidenced by tests conducted on mice. Male $CF_1$ mice obtained from Charles River Breeding Laboratories, fasted for 16-22 hours and weighing 18-22 g at the time of testing are used throughout. All mice are dosed sequentially by the oral route with suspensions of ibuprofen and/or of oxycodone hydrochloride solutions. A dosing volume of 10 ml/kg is used for each sequential solution or suspension. All doses are coded and the test is performed under a code not known to the observer.

A stock suspension of ibuprofen is prepared by mixing 251.4 mg ibuprofen with 70 ml of an aqueous vehicle containing 2% by volume of Tween 80 ®, a pharmacological dispersant manufactured by Fisher Scientific Company and containing 100% polysorbate 80, and 0.25% by weight of Methocel ® A15C powder, a suspending agent manufactured by DOW Chemical Company and containing 100% methylcellulose, in distilled water. The mixture is sonicated at 150 watts for 1-2 minutes with an ultrasound system, then shaken for two hours at 280 oscillations/minute with 15-20 gm of glass beads. The resultant suspension contains 3.59 mg/ml of ibuprofen; all dosing suspensions are prepared by dilution of the stock suspension with the Methocel®/Tween 80® vehicle; the vehicle control is Methocel®/Tween 80®. All suspensions are prepared fresh daily.

Stock solutions of oxycodone HCl are prepared by dissolving dry oxycodone hydrochloride powder with the Methocel®/Tween 80® vehicle. All dosing solutions are prepared by dilution of the stock solution with the Methocel®/Tween 80® vehicle; the vehicle control is Methocel®/Tween 80®.

As indicated above, the standard procedure based upon the prevention of phenyl-p-benzoquinone induced writhing in mice is utilizecd to detect and quantify the analgesic activity of compositions containing oxycodone and ibuprofen.

Mice, intubated with various doses of oxycodone hydrochloride, ibuprofen, combined doses of oxycodone hydrochloride and ibuprofen, or vehicle, are injected intraperitoneally with a challenge dose of phenyl-p-benzoquinone 5 minutes prior to the designated observation period. The phenyl-p-benzoquinone is prepared as an 0.1 mg/ml solution in 5% by volume of ethanol in water; the writhing dose is 1.25 mg/kg injected in a volume of 0.25 ml/20g. For scoring purposes a "writhe" is indicated by whole body stretching or contraction of the abdomen; mice are observed 10 minutes for the presence or absence of writhing beginning 5 minutes after receiving the phenyl-p-benzoquinone dose. Each mouse is used only once, then discarded. The alleviation of pain is quantified by determining the dosage at which 50% of the mice in a test group exhibit an analgesic response for the compsition being tested. This dosage as described herein is referred to as the ED50. All ED50 values and their 95% confidence limits are determined numerically by the computer-assisted methods of Finney. [D. J. Finney, "Probit Analysis", Third Edition, Cambridge University Press, Cambridge, England, 1971].

In order to study the interaction between oxycone and ibuprofen, 5 precise dosage ratios of oxycodone hydrochloride and ibuprofen are selected. Four or five coded doses of each selected combination are studied for analgesic effectiveness at 5 minutes using an experimental design which permits coding and complete randomization of the separate dosage forms tested. Altogether 35 separate dosage forms are used and each form is represented in each experimental session. The experiments are continued by running experimental sessions with an equal number of mice per group being tested until the total number, N, of mice tested per group is 21. Later, an additional 22 mice/dose are tested at all dose ratios and the results are pooled with the original data to yield N=43 mice/dose.

The nature of the analgesic interaction (addition, synergism, or antagonism) is determined by graphing the results in a Loewe isobologram [S. Loewe, *Pharm. Rev.* 9:237-242 (1957)]. The isobologram is a quantitive method for measuring interactions between drugs where dose-effect relationships are depicted in a multi-dimensional array with lines connecting dose pairs that are equieffective in relationship to a common pharmacological endpoint. In this instance, the antiphenylquinone writhing test is used to estimate a common level of analgesic activity (ED50dose) for the two component drugs separately and for each fixed dose-ratio combination. In the isobolographic figure, areas of dose addition, synergism, and/or antagonism are clearly defined by reference to the theoretical "ED50 Addition Line." According to Loewe's isobolographic theory, ED50's falling under the curve (between the ED50 Addition Line and the origin) would represent unexpectedly enhanced analgetic activity and combination ED50's located above the line would represent unexpectedly diminished analgetic activity.

Most importantly, the isobolographic technique permits a full range of doses and dose combinations to be examined where the proportion of the first drug to the second actually varies from 0 to infinity, and to determine, by virtue of the graphical display, whether any one or more of the paired drug combinations displays unique pharmacological properties in comparison to the entire body of data generated. The isobologram is also valuable for organizing the data in a form which is easily amenable to statistical assessment of observed differences.

The synergistic interaction of oxycodone hydrochloride and ibuprofen on phenyl-p-benzoquinone induced writhing in mice is demonstrated by the data in Table I and in the FIGURE, the Loewe isobologram. In the isobolographic figure, the analgesic effect of oxycodone alone is presented in the ordinate, and that of ibuprofen alone is on the abscissa. The dotted lines radiating from the origin represent the exact fixed dosage ratios based on weight of oxycodone HCl:ibuprofen in the ranges of 1:1.25 to 1:31.1. ED50 values are marked on the ordinate and abscissa, representing oxycodone and ibuprofen alone, and on the dotted radial lines, representing the compositions of oxycodone and ibuprofen at the fixed dosage ratios. The arrows extending above and below each ED50 point represent the 95% confidence limits of the ED50's.

As drawn in the FIGURE, the solid diagonal line joining the ED50 values of the two drugs given separately represents the "ED50 Addition Line," the theoretical line for simple additivity of drug effects which would be observed in the absence of a synergistic response. The drawing clearly shows that in the method of the invention, all of the tested fixed ratio compositions give unexpectedly enhanced analgetic activity since the ED50 values for each of these ratios fall below the line of simple additivity.

By utilizing an equieffective dose substitution model and a statistical regression analysis of all of the data, one can obtain a more reliable assessment of the existence of a synergistic property, in this case unexpectedly enhanced analgesic activity. The effects of two compounds are additive if the response to a dose of the two in combination does not change when a portion of one is removed from the mixture and replaced by an equipotent portion of the other. If such substitution increases the response, the mixing together of the compounds is said to potentiate their effect and synergism exists.

Consider ED50 doses of mixtures of X units of compound B with Y units of compound A, whose ED50 doses are $\beta$ and $\alpha$, respectively. Given the hypothesis of additivity, all doses of mixtures satisfying the straight line relation, $$Y = \alpha - \frac{\alpha}{\beta} X,$$

will be ED50 doses. To test the hypothesis of additivity, ED50 doses of mixtures are estimated through probit analysis of data from experiments run at various ratios of A to B. Linear and curvilinear regression models are fitted to the data to estimate the amounts of A in respective ED50 doses, given the amount of B, (or, conversely, the amount of B, given A). If a curvilinear regression fit the data significantly better than a straight line regression, the hypothesis of additivity is refuted and synergism exists for the two compounds for the property of interest.

Values of Y calculated from the straight line of Equation 1, and values of Y calculated from the curvilinear regression are plotted against X on an ED50 isobologram to describe the synergism.

It is convenient to standardize the units of dose such that 100 units of either compound alone is its respective estimated ED50 dose. The additivity hypothesis, then, will be represented by a straight line from 100 on the Y-axis to 100 on the X-axis on the isobologram, and Equation (1) becomes:

$$Y = 100 - X.$$

The isobologram in the FIGURE shows the straight line additivity hypothesis for oxycodone HCl and ibuprofen five minutes post oral dosing in the mouse antiphenylquinone writhing test. Data are standardized to the ED50 doses of oxycodone HCl (1.88 mg/kg) and ibuprofen (15.8 mg/kg). Synergism is demonstrated by the regression fitted to ED50 dose levels estimated by probit analysis. Its curvilinearity is statistically significant.

The regression is fitted to the data by the method of least squares. Residual squared deviations about the line of best fit are minimized in directions along lines from the origin through respective data points on the isobologram, these lines making angles with X-axis, $\tan^{-1}(Y/X)$. This is accomplished by a transformation prior to the regression analysis. Its inverse is applied to transform the coordinates of the regression curve back to the X,Y coordinates of the isobologram.

Let $D_r$ be an ED50 dose of a mixture of A and B, where r is the fraction of compound B in the mixture; i.e.

$$r = \frac{X}{X + Y}.$$

It follows from Equation 1 that $$D_r = \frac{\alpha\beta}{\alpha r + \beta(1 - r)}.$$

From the additivity hypothesis, the logarithms of the ED50 doses at various mixture ratios are a straight line function of (Log $D_r$). To test the hypothesis, polynomial regressions, as follows, are fitted to ED50 estimates from experimental data obtained at various mixture ratios:

$$F_r = \log D_r = b_0 + \sum_{i=1}^{K} b_i \left( \log \left[ \frac{\alpha\beta}{\alpha r + \beta(1 - r)} \right] \right)^i \quad (2)$$

The additivity hypothesis is refuted if a polynomial of degree higher than one fit the data significantly better than a straight line.

$$F_r = b_0 + b_1 \left[ \log \left( \frac{\alpha\beta}{\alpha r + \beta(1 - r)} \right) \right]$$

Since X and Y are uniquely determined by $F_r$ and r, the coordinates of the regression are transformed readily to the coordinates of the isobologram.

If data are scaled to ED50 dose levels of 100 standard dose units, Equation (2) becomes $$F_s = \log 100 = 2. \quad (2.1)$$

The additivity hypothesis implies that $F_s$ is independent of $r_s$, and may be tested by analysis of the regression model $$F_s = b_0 + \sum_{i=1}^{K} b_i r_s^i, \quad (2.2)$$

the subscripts, s, indicating that the data are scaled. A statistically significant regression will refute the hypothesis.

The method of least squares utilizes jointly the information contained in all of the separate data points. Statistical significance of the curvilinearity of the regression model establishes the existence of synergism (or antagonism) of the compounds in the biological system studied. The parameters in the model describe its intensity over the range of mixture ratios, from 0 to 1, the nature of which is seen readily when the regression is plotted on the isobologram. This method was used to determine the best-fitting ED50 regression line through the seven (7) ED50 data points representing equivalent levels of analgetic activity for each of the five (5) dose-ratios and for oxycodone and ibuprofen alone given in Table I. As shown in the isobologram plot of the FIGURE, the calculated quadratic polynomial "ED50 Regression Line" fits the data significantly better than the straight "ED50 Addition Line" using stringent, 95% confidence limits (P<0.016). Thus, consistent with Loewe's isobolographic model, the hypothesis of analgesic additivity is refuted and analgesic synergism is established for all combinations of oxycodone and ibuprofen.

By substitution of the expected analgesic activity of oxycodone alone and ibuprofen alone from test results in other warm blooded mammals, it is possible to use the isobologram in conjunction with the correlation method discussed above to predict the equivalent range of maximum potentiating dosages for man. Thus, utilizing the data of the present invention and the equivalent ratios in man, it is predicted that oxycodone and ibuprofen would demonstate analgetic potentiation over a range of doses exceeding 1:1 to 1:800. Within this range, doses of 1:3 to 1:400 are preferred while doses of 1:6 to 1:400 are most preferred. Based on the above results with oxycodone showing synergism over a broad compositional range, one skilled in the art would project synergism with other narcotic analgesics, particularly oxymorphone, hydrocodone, and hydromorphone which are all potent orally in man in the range of about 1 mg ot 10 mg per dose.

As described above, all tests of statistical significance establishing the best fit regression equation for the experimental data and its difference from the ED50 Addition Line were carried out using stringent 95% confidence limits. The use of less stringent limits merely reinforces the conclusions.

2. The pharmaceutical composition of claim 1 in oral dosage form.

3. The pharmaceutical composition of claim 1 which contains in addition a suitable pharmaceutical carrier.

4. A method of alleviating pain in a mammal which comprises administering to said mammal affected with pain an effective analgesic amount of the composition of claim 3.

5. A method of alleviating pain in a mammal which comprises administering to said mammal affected with

TABLE 1

ORAL OXYCODONE HCl/IBUPROFEN COMBINATIONS IN THE MOUSE ANTIPHENYLQUINONE WRITHING TEST
5 Min. (N = 43 Mice/Dose)

| DRUG COMBINATIONS Oxycodone: Ibuprofen | DRUG DOSE (mg/kg) | | % MICE BLOCKED | ED50 AT 5 MIN (95% Confidence Limits) | |
|---|---|---|---|---|---|
| | Oxycodone | Ibuprofen | | Oxycodone | Ibuprofen |
| Control (0:0) | 0 | 0 | 4.7 | — | — |
| Oxycodone | 0.36 | 0 | 11.6 | | |
| Only (1:0) | 0.72 | 0 | 4.7 | | |
| | 1.44 | 0 | 39.5 | 1.88 | 0.0 |
| | 2.88 | 0 | 81.4 | (1.52–2.23) | |
| | 5.76 | 0 | 95.3 | | |
| 1:1.25 | 0.3 | 0.37 | 14.0 | | |
| | 0.6 | 0.75 | 16.3 | | |
| | 1.2 | 1.50 | 32.6 | 1.54 | 1.92 |
| | 2.4 | 2.99 | 88.4 | (1.25–1.81) | (1.55–2.26) |
| | 4.8 | 5.99 | 97.7 | | |
| 1:3.12 | 0.24 | 0.75 | 11.6 | | |
| | 0.48 | 1.50 | 20.9 | | |
| | 0.96 | 2.99 | 41.9 | 1.08 | 3.33 |
| | 1.92 | 5.99 | 86.0 | (0.861–1.29) | (2.66–3.96) |
| | 3.84 | 11.97 | 100.0 | | |
| 1:6.24 | 0.18 | 1.12 | 4.7 | | |
| | 0.36 | 2.25 | 20.9 | | |
| | 0.72 | 4.49 | 41.9 | 0.733 | 4.57 |
| | 1.44 | 8.98 | 93.0 | (0.598–0.868) | (3.73–5.42) |
| | 2.88 | 17.96 | 97.7 | | |
| 1:12.5 | 0.12 | 1.50 | 11.6 | | |
| | 0.24 | 2.99 | 30.2 | | |
| | 0.48 | 5.99 | 44.2 | 0.460 | 5.75 |
| | 0.96 | 11.97 | 86.0 | (0.356–0.565) | (4.45–7.07) |
| | 1.92 | 23.95 | 97.7 | | |
| 1:31.1 | 0.06 | 1.87 | 7.0 | | |
| | 0.12 | 3.74 | 16.3 | | |
| | 0.24 | 7.48 | 39.5 | 0.321 | 9.98 |
| | 0.48 | 15.0 | 72.1 | (0.249–0.399) | (7.76–12.4) |
| | 0.96 | 29.9 | 88.4 | | |
| Ibuprofen | 0 | 2.25 | 7.0 | | |
| Only (0:1) | 0 | 4.49 | 11.6 | 0.0 | 15.8 |
| | 0 | 8.98 | 20.1 | | (12.8–21.0) |
| | 0 | 17.96 | 62.8 | | |

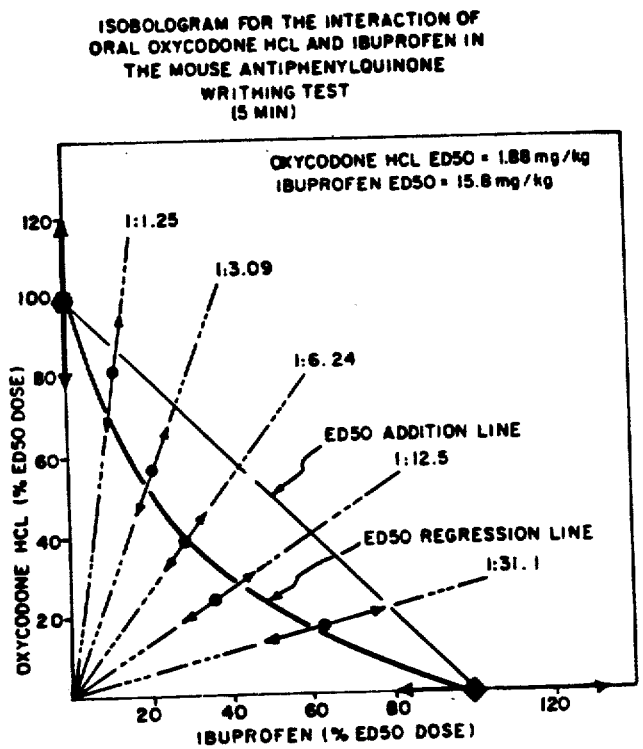

What is claimed is:

1. A pharmaceutical composition comprising a synergistic analgesic combination of (a) oxycodone, or a pharmaceutically acceptable salt thereof, and (b) ibuprofen, or a pharmaceutically suitable salt thereof, in which the weight ratio of (a):(b) is from about 1:6 to about 1:400.

pain an effective analgesic amount of the composition of claim 1.

6. A method of alleviating pain in a mammal which comprises administering to said mammal affected with pain an effective analgesic amount of the composition of claim 2.

* * * * *

UNITED STATES PATENT AND TRADEMARK OFFICE
CERTIFICATE OF CORRECTION

PATENT NO. : 4,569,937  Page 1 of 2
DATED : February 11, 1986
INVENTOR(S) : Geraldine Lee Baker et al.

It is certified that error appears in the above-identified patent and that said Letters Patent is hereby corrected as shown below:

The title page showing the illustrative figure should appear as shown on the attached sheet.

Column 9, line 19, "utilizecd" should read -- utilized --.
Column 9, line 45, "oxycone" should resd -- oxycodone --.
Column 13, line 4, "1mg ot 10mg" should read -- 1mg to 10mg --.

Signed and Sealed this

Thirteenth Day of May 1986

[SEAL]

Attest:

DONALD J. QUIGG

Attesting Officer            Commissioner of Patents and Trademarks

United States Patent [19]

Baker et al.

[11] Patent Number: 4,569,937

[45] Date of Patent: Feb. 11, 1986

[54] ANALGESIC MIXTURE OF OXYCODONE AND IBUPROFEN

[75] Inventors: Geraldine L. Baker, Minneapolis, Minn.; William K. Schmidt, Wilmington, Del.

[73] Assignee: E. I. Du Pont de Nemours and Company, Wilmington, Del.

[21] Appl. No.: 700,654

[22] Filed: Feb. 11, 1985

[51] Int. Cl.$^4$ .................... A61K 31/19; A61K 31/44
[52] U.S. Cl. .................... 514/282; 514/557
[58] Field of Search ........................ 424/260

[56] References Cited

U.S. PATENT DOCUMENTS 4,322,427  3/1982  Buyniski et al.
4,489,080  12/1984  Loman ........................ 424/260

FOREIGN PATENT DOCUMENTS 0068838  1/1983  European Pat. Off.

OTHER PUBLICATIONS

S. A. Cooper et al., "Relative Efficacy of an Ibuprofen-Codeine Combination", Clin. Pharmacol. Ther., 27(2), 1980, p. 249.

AMA Drug Evaluations, Fifth Ed., 1983 Chapter 4, pp. 101–102.

Pharmacotherapy, 2, No. 3, May/Jun. 1982, Cooper et al.: Analgesic Efficacy of an Ibuprofen-Codeine Combination, pp. 162–167.

Clinical Pharmacology, K. L. Melmon, M.D., et al., Chap. 11, pp. 498–499, (1972).

The Pharmacological Basis of Therapeutics, L. S. Goodman et al., 5th Ed., Chap. 17, pp. 348–349, (1975).

*Primary Examiner*—Stanley J. Friedman

[57] ABSTRACT

Pharmaceutical compositions of narcotic analgesics and ibuprofen have been found to exhibit unexpectedly enhanced analgesic activity by applying an analysis model which considers data characterizing the analgesic effect of both the pure components as well as the fixed dose ratio combinations. This synergism enables the use of lower doses of either or both drugs with a concomitant reduction in risk of possible side effects.

6 Claims, 1 Drawing Figure